(12) United States Patent
Gorski et al.

(10) Patent No.: US 8,425,996 B2
(45) Date of Patent: Apr. 23, 2013

(54) INDICATORS FOR DETECTING THE PRESENCE OF METABOLIC BYPRODUCTS FROM MICROORGANISMS

(75) Inventors: Joel R. Gorski, Perrysburg, OH (US); Jon Booher, Advance, NC (US); Ram W. Sabnis, Morris Plains, NJ (US)

(73) Assignee: Indicator Systems International, Inc., San Clemente, CA (US)

( * ) Notice: Subject to any disclaimer, the term of this patent is extended or adjusted under 35 U.S.C. 154(b) by 387 days.

(21) Appl. No.: 12/693,375

(22) Filed: Jan. 25, 2010

(65) Prior Publication Data

US 2010/0196636 A1 Aug. 5, 2010

Related U.S. Application Data

(60) Provisional application No. 61/147,450, filed on Jan. 26, 2009, provisional application No. 61/258,515, filed on Nov. 5, 2009, provisional application No. 61/269,961, filed on Jun. 30, 2009, provisional application No. 61/297,234, filed on Jan. 21, 2010.

(51) Int. Cl.
- *A61K 9/70* (2006.01)
- *B32B 27/32* (2006.01)
- *B32B 27/08* (2006.01)
- *B32B 37/12* (2006.01)
- *B32B 3/00* (2006.01)
- *A61P 31/04* (2006.01)
- *G01N 33/00* (2006.01)
- *C12Q 1/04* (2006.01)

(52) U.S. Cl.
USPC ....... 428/35.7; 428/195.1; 428/521; 424/445; 435/34; 156/60; 252/408.1

(58) Field of Classification Search .......... None
See application file for complete search history.

(56) References Cited

U.S. PATENT DOCUMENTS

| | | |
|---|---|---|
| 3,899,295 A | 8/1975 | Halpern |
| 3,946,611 A | 3/1976 | Larsson |
| 4,094,642 A | 6/1978 | Sumimoto et al. |
| 4,197,947 A | 4/1980 | Zaidi |
| 4,205,043 A | 5/1980 | Esch et al. |
| 4,222,745 A | 9/1980 | Cloyd |
| 4,269,804 A | 5/1981 | Kring |
| 4,271,121 A | 6/1981 | Diller et al. |
| 4,285,697 A | 8/1981 | Neary |
| 4,328,181 A | 5/1982 | Anders et al. |
| 4,746,616 A | 5/1988 | Honigs et al. |
| 4,987,849 A | 1/1991 | Sherman |
| 5,053,339 A | 10/1991 | Patel |
| 5,096,813 A | 3/1992 | Krumhar et al. |
| 5,128,106 A | 7/1992 | Buschmann et al. |
| 5,215,956 A | 6/1993 | Kawashima |
| 5,228,573 A | 7/1993 | Pavelle et al. |
| 5,407,829 A | 4/1995 | Wolfbeis et al. |
| 5,437,622 A | 8/1995 | Carion |
| 5,498,528 A | 3/1996 | King |
| 5,629,360 A | 5/1997 | Askari et al. |
| 5,753,285 A | 5/1998 | Horan |
| 5,916,585 A | 6/1999 | Cook et al. |
| 5,922,281 A | 7/1999 | Elgas et al. |
| 6,149,614 A | 11/2000 | Dunshee et al. |
| 6,149,952 A | 11/2000 | Horan |
| 6,391,626 B1 | 5/2002 | Adams et al. |
| 6,495,368 B1 | 12/2002 | Wallach |
| 6,562,297 B1 | 5/2003 | Bonstein et al. |
| 6,589,761 B1 | 7/2003 | Freadman et al. |
| 6,924,147 B2 | 8/2005 | Kelly et al. |
| 7,014,816 B2 | 3/2006 | Miller et al. |
| 7,183,455 B2 | 2/2007 | Utsugi |
| 7,749,531 B2 | 7/2010 | Booher |
| 2003/0060479 A1 | 3/2003 | Brown et al. |
| 2003/0064422 A1 | 4/2003 | McDevitt et al. |
| 2003/0199783 A1 | 10/2003 | Bloom et al. |
| 2003/0203011 A1 | 10/2003 | Abuelyaman et al. |
| 2004/0043422 A1 | 3/2004 | Ferguson et al. |
| 2004/0044299 A1 | 3/2004 | Utsugi |
| 2004/0076662 A1 | 4/2004 | Riesinger |
| 2004/0115319 A1 | 6/2004 | Morris et al. |
| 2006/0134728 A1* | 6/2006 | MacDonald et al. ........... 435/34 |
| 2006/0222675 A1* | 10/2006 | Sabnis et al. .................. 424/405 |
| 2007/0003606 A1* | 1/2007 | Booher ......................... 424/448 |
| 2007/0123810 A1 | 5/2007 | Utsugi et al. |
| 2007/0276207 A1 | 11/2007 | Eagland et al. |
| 2010/0279339 A1 | 11/2010 | Booher |
| 2011/0042344 A1 | 2/2011 | Booher et al. |
| 2011/0274593 A1 | 11/2011 | Gorski et al. |

FOREIGN PATENT DOCUMENTS

| | | |
|---|---|---|
| IE | 20040542 | 2/2006 |
| WO | WO-99/59431 | 11/1999 |
| WO | WO-2006/133430 | 12/2006 |
| WO | WO-2009/061831 | 5/2009 |
| WO | WO-2010/085755 | 7/2010 |

OTHER PUBLICATIONS

Lambert et al. "Improved Synthesis of Polymethoxytriphenyl-methanols fo ruse as One-colour PH Indicators." *Analyst.* 1981, 106:1013-1016.

U.S. Appl. No. 12/637,552, filed Dec. 14, 2009, Booher et al.

Liu et al., "Facile Synthesis, Characterization, and Potential Applications of Two Kinds of Polymeric pH Indicators: Phenolphthalein Formaldehyde and o-Cresolphthalein Formaldehyde." Journal of Polymer Science, 2005, 43:1019-1027.

Rubin et al., "The Economic Impact of *Staphylococcus aureus* Infection in New York City Hospitals: Emerging Infectious Diseases." Emerging Infectious Diseases, (1999) 5(1):9-17.

Soken Chemical and Engineering Co., Ltd., http://www.soken-ce.co.jp/english/nencyaku/lineup-index.html, archived web pages from 2004 for SK Dyne pressure-sensitive adhesives, printed from the Internet on Mar. 11, 2009.

\* cited by examiner

*Primary Examiner* — Robert A Wax
*Assistant Examiner* — Randeep Singh
(74) *Attorney, Agent, or Firm* — Foley & Lardner LLP

(57) ABSTRACT

Polymeric indicator films and pH indicating wraps are provided for visually monitoring, detecting, and/or determining the presence of metabolic byproducts from harmful or potentially harmful microorganisms. Also provided are methods of use and preparation of the polymeric indicator films.

6 Claims, 3 Drawing Sheets

INDICATORS FOR DETECTING THE PRESENCE OF METABOLIC BYPRODUCTS FROM MICROORGANISMS

CROSS-REFERENCE TO RELATED APPLICATIONS

This application claims the benefit under 35 U.S.C. §119 (e) to U.S. provisional application Ser. Nos. 61/147,450, filed Jan. 26, 2009, 61/258,515, filed Nov. 5, 2009, 61/269,961, field Jun. 30, 2009, and 61/297,234, filed on Jan. 21, 2010. All of which are incorporated hereby by reference in their entirety.

TECHNICAL FIELD

This invention relates generally to polymeric indicator films useful, for example, in pH indicating food wraps and wound dressings, This invention is also directed to uses of these films for detecting the presence of bacterial growth as measured by bacterial growth by-products. Such by-products alter the pH of an aqueous composition in contact with the film.

BACKGROUND

The presence of undesirable bacterial contamination in food products intended for consumption is of significant concern to manufacturers, farmers, packagers, food distributors, wholesalers, retailers, consumers, and to worldwide public health. A particularly worrisome concern is bacterial contamination in packages containing food products for human consumption. The United States boasts of the safest food in the world; however, each year approximately one in four individuals suffer from a food borne illness and some 5,000 die from something they have eaten. According to the Center for Disease Control and Prevention, each year in the United States, 76 million people contract some kind of food borne illness, 325,000 are hospitalized and 5,000 fatalities occur due to contamination of consumed food. In Third World countries it has been estimated that bacterial contaminated food and water kills over two million children each year. Despite those numbers, most food borne infections are undiagnosed and unreported.

Packaging of perishable and edible food products may be susceptible to undesired and undetectable bacterial growth during each stage in the food chain from harvest to consumption. Minimal levels of bacterial contamination (bacterial load) of food is deemed acceptable in food for consumer use. Indeed, regulatory agencies such as the FDA have established limits on bacterial load permitted in the food. Nevertheless, it is very hard to determine if bacterial growth in food alters the bacterial level of the food to unacceptable levels. Food initially safe for consumption may be altered by undetected bacterial growth due to poor handling, improper storage and other factors. At all points in the food chain, it would be of great benefit if there was an unmistakable means to determine that there has been unacceptable bacterial growth occurring on the food.

Still further, bacterial contamination of wounds can lead to serious infection, illness, and even death if the contamination is unnoticed and untreated for even a relatively short period of time. Often times, bacterial infection is first detected by the presence of inflamed red skin around a wound site. Visualization of the wound by skin redness is often at a point where the infection has significantly progressed within the diseased patient.

Examples of such wounds are those generated by use of central venous catheters, cannulae, and related medical devices (hereafter "catheters") which are inserted and maintained through the skin. As is apparent, catheters are used on a variety of patients, usually in a hospital setting. These catheters provide secure access e.g., into a patient's blood vessel and allow for the safe administration of fluids and drugs into the patient or the removal of fluids from the body.

Wounds of all nature carry an inherent risk of bacterial infections. In addition to intentionally created wounds such as those described above, other wounds susceptible to infection include abrasions, burns, surgical incisions, injection sites, and the like.

For example, catheter insertion into the body can cause serious complications. Specifically, catheter related bloodstream infection (CR-BSI) is a serious and potentially life-threatening complication when catheter insertion sites into blood vessel lumen become infected with bacterial microorganisms. Conventional state of the art care now requires that these insertion sites be covered with a wound dressing as a preventive measure against such infections.

A number of factors render such insertion sites especially susceptible to bacterial contamination. Specifically, the catheter essentially compromises the skin's natural protective barrier, providing a direct route to bypass the body's first line of immunity. In addition, upon insertion into the host, the outer surface of the catheter is quickly covered with host proteins that facilitate bacterial attachment and growth. There is also evidence that implanted abiotic material itself causes local attenuation of antimicrobial immune responses, thereby inhibiting a normal immune response against bacterial biofilm formation. Finally, patients who possess the greatest need for catheterization are often immunologically compromised and are therefore more susceptible to bacterial infection.

Catheters themselves are generally infected via one of two general routes, typically by microorganisms that compromise the natural flora surrounding the site of catheter insertion. For example, bacteria may contaminate the catheter along its outer surface, and it is believed that this type of infection often occurs during the initial insertion of the catheter through the skin. Catheters can also be contaminated in their lumenal compartments where fluids flow from contaminated infusate solutions. The most prevalent bacteria found to be the cause of bacterial sepsis are from the exterior flora surrounding the insertion site.

Catheter-related bloodstream infections are notoriously difficult to treat via conventional antibiotic therapy, with associated mortality rates ranging from 12% to 25%. Catheter related bloodstream infection is the most frequent serious complication seen with catheters with infections occurring in as many as 3% to 7% of all catheter placements, which is estimated to affect more than 250,000 patients in U.S. hospitals each year. In addition, these infection complications extend hospital stays, necessitate active intervention on the part of healthcare personnel, and result in driving the estimated annual domestic healthcare cost associated with complications arising from these catheter-related infections to more than nine billion dollars.

The use of a wound covering (sometimes referred to as a "dressing" or "wound dressing") in conjunction with a catheter is conventional but does not entirely obviate the underlying infection risk as evidenced by the statistics above. Such wound dressings are typically placed proximate the catheter injection site and contact fluids exuding from that site.

Still further, other wounds such as burns, abrasions, surgical incisions, and the like are particularly susceptible to infection. In hospital settings, infections caused by antibiotic resistant bacteria such as *Staphylococcus* is a major concern and a cause of morbidity.

Therefore, a need exists for methods and medical devices and wound coverings for the detection of bacterial growth contamination in or about a wound that can readily detect and indicate the presence of microorganisms well before the infection has progressed to the point that it manifests itself by skin redness.

SUMMARY OF THE INVENTION

In one aspect, this invention relates to a polymeric indicator film comprising a transparent and uncolored polymer layer or layers and a plurality of pH indicating moieties, wherein the pH indicating moieties are entrapped within the polymer layer or between two or more of the polymer layers and further wherein the pH indicating moieties retain the transparency and lack of color of the polymer film at neutral pH but which impart color to at least a portion of the film when exposed to an acidic pH.

In another aspect, this invention provides a "sandwich" type of polymeric indicator film comprising:
 a) a first layer comprising one or more hydrophilic, hydronium ion penetrating layers;
 b) a second layer comprising one or more hydrophobic, water impermeable layers; and
 c) a pH indicator layer placed between the first layer and second layer.

In some embodiments, the polymeric indicator film is for detecting the presence of bacterial growth in food. In some embodiments, the polymeric indicator film is for detecting the presence of bacterial growth in or around a wound.

In some embodiments, the pH indicating moieties are selected from heptamethoxy red and hexamethoxy red or a combination thereof. These indicators are particularly useful as when used in an amount to detect pH change in either food or bodily fluids, they retain the transparent and uncolored nature of the polymeric indicator film at a neutral pH. However, when the pH becomes acidic (due to by-products of bacterial growth), the color of the indicator film becomes red. This permits ready determination that bacterial growth has occurred.

In another aspect, there is provided a process for preparing a polymeric indicator film comprising a first hydrophilic, hydronium ion penetrating transparent layer and a second hydrophobic, water impermeable transparent layer which process comprises:
 a) selecting one or more hydrophilic, hydronium ion penetrating layers as the first layer of the polymeric film wherein the first layer has a front and back surface;
 b) selecting one or more hydrophobic, water impermeable layers as the second layer of the polymeric film wherein the second layer has a front and back surface;
 c) applying a pH indicator layer to at least a portion of one surface of the second layer; and
 d) bonding the first and second layers together such that the pH indicator layer is placed between the first and second layers,
wherein the pH indicator layer comprises hexamethoxy red and/or heptamethoxy red or derivatives thereof.

Other embodiments of the invention are further described in the Detailed Description that follows.

BRIEF DESCRIPTION OF THE DRAWINGS

It should be appreciated that like reference numerals are used to identify like elements illustrated in one or more of the figures. It should also be appreciated that the figures may not be necessarily drawn to scale.

DETAILED DESCRIPTION OF THE INVENTION

Figure 1:
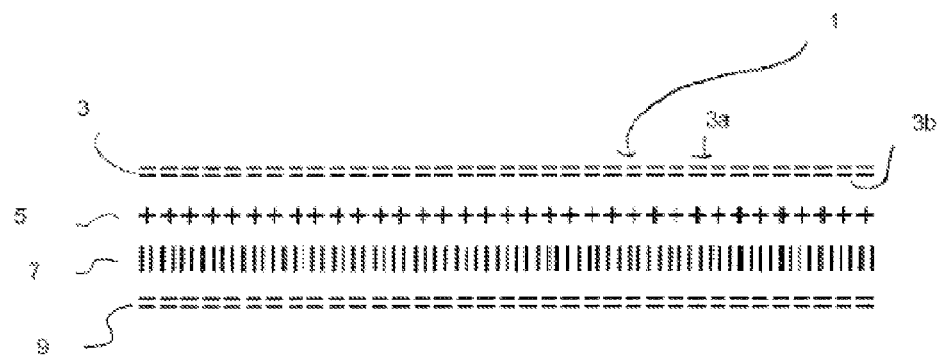
FIG. 1 illustrates one example of a polymeric indicator film of this invention.

Throughout this application, the text refers to various embodiments relating to compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present invention.

Definitions

As used herein, certain terms may have the following defined meanings. As used in the specification and claims, the singular form "a," "an" and "the" include singular and plural references unless the context clearly dictates otherwise.

The term "comprising" is intended to mean that the compounds and methods include the recited elements, but not excluding others. "Consisting essentially of" when used to define compositions and methods, shall mean excluding other elements of any essential significance to the compounds or methods. "Consisting of" shall mean excluding more than trace elements of other ingredients for claimed compounds and substantial method steps. Embodiments defined by each of these transitional terms are within the scope of this invention. Accordingly, it is intended that the processes and compositions can include additional steps and components (comprising) or alternatively include additional steps and compounds of no significance (consisting essentially of) or alternatively, intending only the stated methods steps or compounds (consisting of).

The term "polymeric indicator film" refers to a polymeric film comprising one or more pH indicator moieties incorporated therein which is able to indicate the presence of a threshold level of bacterial by-products by a visible color change. In some embodiments, the polymeric indicator film comprises a hydrophilic, hydronium ion penetrating layer and a hydrophobic, water impermeable layer. In some embodiments, the hydrophilic, hydronium ion penetrating layer contains a plurality of pH indicator moieties embedded therein. In some embodiments, the pH indicator moieties are positioned between the hydrophobic, water impermeable layer and the hydrophilic, hydronium ion penetrating layer optionally by use of an adhesive.

Neutral pH has a value of 7.0. As used herein, the term "neutral pH" also includes low acid pH of from about 5 to below 7 and low basic pH of from above 7 to up to about 8.

The term "acidic" as used herein refers to an acidic pH range generally produced from by-products of bacterial growth. Such acidic pHs generally range from above 1 to about 5 and, preferably, a pH range of from 2 to about 5. A strong acid has a pH of below 2.0.

The term "transparent layer" refers to a polymer layer which is sufficiently transparent to visible light that a viewer can readily see through the layer. Preferably, the transparent layer is uncolored (as that term is defined below).

The term "hydrophobic, water impermeable layer" refers to a transparent polymer layer wherein the polymer is hydrophobic and does not permit water, water vapor, bacteria or protons (hydronium ions) to readily penetrate into or through the layer. Especially preferred hydrophobic, water impermeable layers are those which qualify as food grade and/or medical grade polymers. In some embodiments, the hydrophobic, water impermeable polymer is polyethylene (PE). In some embodiments, that polymer includes, but is not limited to, polyvinylalcohol, polyethylene terephthalate, poly(vinylidene fluoride), poly(vinyl chloride), poly(vinylidene chloride), polypropylene, phenoxy resins, butadiene/styrene copolymers, butadiene/methylstyrene copolymers, poly (meth)acrylates, butadiene/acrylonitrile copolymers, ethylene/propylene copolymers, polybutadiene, polyisoprene, poly(oxy-2,6-dimethyl-1,4-phenylene), poly(oxycarbonyloxy-1,4-phenyleneisopropylidene-1,4-phenylene), acrylonitrile styrene copolymers, acrylonitrile/methyl acrylate/ butadiene copolymers, acrylonitrile/styrene/butadiene copolymers, poly-1-vinylnaphthalene, polyvinylphenyl ketone, poly-p-xylenedodecanedioate, poly-tetramethylene octenediamide, poly-tetramethylene terephthalene, poly-trimethylene-3,3'-dibenzoate, poly-terephthallic anhydride, poly-4-methyl-diamine, polyvinylene carbonate, polyvinylene laurate, polyisopropenyl acetate, polyallylbenzene, polyvinylbutyl ether, polyvinyl formate, polyvinyl phenyl ether, polynorbornadine, polycarbonate, hydrophobic polyesters and polyurethanes, or a mixture thereof.

The term "barrier membrane" is synonymous with "hydrophobic, water impermeable layer" and is sometimes used herein relative to the polymer layer over a wound dressing to prevent water or water vapor or bacteria from penetrating through that layer from the environment and contacting the wound site.

The term "hydrophilic, hydronium ion penetrating layer," which is sometimes referred to herein as a "hydrophilic, hydronium ion permeable layer," refers to a transparent polymer layer wherein the polymer is hydrophilic and permits water, water vapor, gases and protons (hydronium ions) to diffuse into or through this polymeric layer which causes increase of the hydronium ion concentration and decrease of the pH. Proton penetration can be determined by a number of measures but is most easily measured by the use of a pH indicator which detects the presence of a sufficient number of protons by a color change. Examples of hydrophilic, hydronium ion penetrating transparent layers include several which are commercially available materials having high moisture vapor transmission rate, such as polyether block amide copolymers (e.g., Pebax®). Preferred hydrophilic, hydronium ion penetrating polymer layers are those which qualify as food grade and/or medical grade polymers. In some embodiments, the hydrophilic, hydronium ion penetrating uncolored transparent layer comprises a polymer selected from the group consisting of polyether block amide (e.g., Pebax®), (poly)hydroxyethyl methacrylate, (poly)hydroxypropyl methacrylate, (poly)glycerol methacrylate, copolymers of hydroxyethyl methacrylate, hydroxypropyl methacrylate or glycerol methacrylate and methacrylate acid, aminoacrylate and aminomethacrylate, (poly)vinyl pyrrolidone, (poly)vinylpyridine, polar polyamides, methyl cellulose, hydroxypropyl cellulose, hydroxyethyl cellulose, hydroxypropyl methylcellulose, ethyl hydroxyethylcellulose, carboxymethyl cellulose, cellulose acetate, cellulose acetate butyrate, cellulose acetate propionate, cellulose nitrate, polyvinyl acetate, polyvinyl alcohol, copolymers of polyvinyl acetate and polyvinyl alcohol, hydroxyl modified copolymers of vinyl acetate and vinyl chloride, polyesters, polyurethanes containing at least about 10% by weight of polyethylene oxide, styrene/methacrylic acid/hydroxyethyl methacrylate copolymers, styrene/methacrylic acid/hydroxypropyl methacrylate copolymers, methylmethacrylate/ methacrylic acid copolymers, ethyl methacrylate/styrene/ methacrylic acid copolymers, ethyl methacrylate/methyl methacrylate/styrene/methacrylic acid copolymers, polytetrafluoroethylene and hydrophilic cellulose copolymers.

The term "permeable membrane" is synonymous with "hydrophilic, hydronium ion penetrating transparent layer" as defined above and is sometimes used to describe the polymer layer of, for example, the wound dressing or the sheath overlaying a catheter at the catheter insertion site that is in contact with body fluids at that site. Permeable gases include but not limited to oxygen, carbon dioxide, carbon monoxide, hydrogen sulfide, hydrogen, sulfur dioxide, and ammonia among others. The permeability of the permeable membrane is such that it permits a sufficient concentration of pH altering gases to diffuse into or through this polymeric layer so as to sufficiently alter the pH and produce a visual colorimetric reaction with the indicator. In some embodiments, the permeable membrane comprises one or more hydrophilic, hydronium ion penetrating transparent layers described above.

The term "bonding" refers the formation of a single polymeric film by adhering two or more separate layers into a single film by conventional techniques.

The term "colorless" refers to the lack of sufficient color so as to be deemed transparent and clear either visually or by instrumentation. When visually evaluated, the term "colorless" does not mean that there is no color but, rather, the color is either not visually detectable or minimally detectable such that the viewer sees a clear film.

The term "colorful" refers to sufficient color such that the color can be detected by visual observation.

The term "threshold level of bacterial by-products" refers to the amount of by-products produced by bacteria such that the pH changes sufficiently to effect a change in the color of the indicator from colorless to colorful. Preferably, the threshold level of bacterial by-products is a level at or below the level produced by a minimum amount of bacteria growth that would cause concern when present on food or at a wound or catheter insertion site.

The term "indicator" refers to a substance capable of changing color with a change in pH caused when a threshold amount of bacterial by-products are produced. In one embodiment, the indicator is a pH indicator. Such pH indicators are sometimes referred to herein as "pH indicating moieties". Bacterial by-products include, but are not limited to, gaseous carbon dioxide, hydrogen sulfide, sulfur dioxide, hydrogen, ammonium, lactate, and mixtures thereof. Mixtures of these by-products with moisture result in the formation of acids such as carbonic acid, sulfuric acid, ammonium hydroxide, lactic acid, or mixtures thereof. When a sufficient amount of acid is generated, the indicator produces a change from uncolored to colored that is readily discernable by even an untrained observer.

Examples of pH indicators include xylenol blue (p-xylenolsulfonephthalein), bromocresol purple (5',5"-dibromo-o-cresolsulfonephthalein), bromocresol green (tetrabromo-m-cresolsulfonephthalein), cresol red (o-cresolsulfonephthalein), phenolphthalein, bromothymol blue (3',3"-dibromothymolsulfonephthalein), p-naphtholbenzein (4-[alpha-(4-hydroxy-1-naphthyDbenzylidene]-1 (4H)-naphthalenone), neutral red (3-amino-7-dimethylamino-2-methylphenazine chloride), hexamethoxy red and heptamethoxy red, and combinations thereof. In a preferred embodiment, the pH indicators are hexamethoxy red and/or heptamethoxy red or derivatives thereof.

The term "bacteria" as used herein refers to any bacteria that may be present in the either food or a wound site regardless of origin and that may further be a potential health hazard. Bacteria detectable by the polymeric indicator films provided herein include *Staphylococcus aureus, Staphylococcus epidermidis, Streptococcus mitis, Streptococcus sanguis, Enterococcus faecium, Escherichia coli, Enterobacter cloacae, Enterobacter aerogenes, Enterococcus faecalis, Pseudomonas aeruginosa, Klebsiella pneumonia, Salmonella, Candida albicans*, gram negative bacilli, or a combination thereof.

The term "catheter" includes any and all known catheters which puncture the skin and are used for delivering fluids, medicaments, etc. into the body, assisting in the elimination of fluids from the body, and/or for diagnostic purposes. Such catheters include central venous catheters, diagnostic catheter, drainage catheters, and the like. Also included within the term "catheter" are cannulae which are conventional, well known, tubes inserted into the body by puncture through the skin, for the delivery or removal of fluids. Cannulae normally come with a trocar which permits puncturing of the body.

The term "food spoilage" refers to the growth of microorganisms, such as bacteria, on food. As used herein, rancidity, which is a breakdown of the cellular matrix of the tissue or meat via protein denaturization process and release of proteins (enzymes) to the extracellular spaces of the tissue, is not detected by the invention.

Polymeric Indicator Films

This invention provides a polymeric indicator film comprising a transparent and an uncolored polymer layer or layers and a plurality of pH indicating moieties, wherein the pH indicating moieties are entrapped within the polymer layer or between one or more of the polymer layers and further wherein the pH indicating moieties retain the transparency of the uncolored polymer film at a neutral pH but which impart color to at least a portion of the film when exposed to an acidic pH.

In some embodiments, the polymeric indicator film is for detecting the presence of bacterial growth in food. In some embodiments, the polymeric indicator film is for detecting the bacterial growth in or around a wound or a catheter insertion site. In particular, one or more embodiments of the invention provide for polymeric indicator films which are colorless in the absence of a threshold level of bacterial growth and colorful when bacterial growth exceeds such a threshold both of which are determined by the generation of by-products of bacterial growth which alter the color of the indicator film.

In another aspect, this invention provides a polymeric indicator film for visually detecting the growth of bacteria, said polymeric indicator film comprising a hydrophilic, hydronium ion penetrating polymer layer and a plurality of pH indicating moieties selected from heptamethoxy red and hexamethoxy red or a combination thereof, wherein the pH indicating moieties are entrapped within the polymer layer. These polymeric indicator films can be employed in situations where the monitoring of bacterial growth is desirable, such as in food or medical settings.

Heptamethoxy red refers to the chemical 2,4,6,2',4',2",4"-heptamethoxytri-phenylcarbinol having Formula (I) below and derivatives thereof which do not alter the ability of the compound to detect changes in pH. Hexamethoxy Red refers to the chemical 2,4,2',4',2",4"-hexamethoxytriphenyl-carbinol having Formula (II) below and derivatives thereof which do not alter the ability of the compound to detect changes in pH.

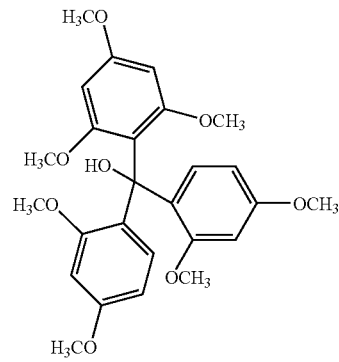

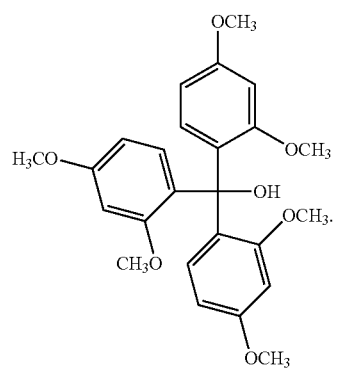

Heptamethoxy red exhibits a dynamic range between approximately pH 7 and pH 5, and hexamethoxy red exhibits a dynamic range between approximately pH 4.5 and pH 2.6. Both exhibit visually perceptible color change from colorless to colorful (reddish/violet red) when exposed to a sufficient amount of acid so as to lower the pH to a level necessary to effect color change. Derivatives of either hexamethoxy red or heptamethoxy red are contemplated to include substitution of one or more of the methoxy groups with a $C_2$-$C_3$ alkoxy group provided that such substitution does not alter the ability of the compound to detect changes in pH.

In some embodiments, the pH indicating moieties are in both gaseous and fluid communication with the bacterial by-products and acids produced therefrom.

In some embodiments, the pH indicating moieties are entrapped within the polymeric film and typically within the hydrophilic, hydronium ion penetrating layer of the polymeric film. General methods for entrapment include those described in U.S. Pat. No. 5,629,360. The pH indicating moieties may also be entrapped within pores in the hydrophilic, hydronium ion penetrating layer. Suitable additives such as diatomaceous earth (DE), $TiO_2$, and $SiO_2$ or combinations thereof may be added to the layer to generate such pores. In some embodiments, the diatomaceous earth is in an amount of up to about 10% w/w. In some embodiments, it is about 4% w/w. In some embodiments, it is about 3% w/w. Pores may also be generated by laser drilling. Weight percents are based on the weight of the additive relative to the weight of the hydrophilic, hydronium ion penetrating layer.

The pH indicating moieties in the polymeric indicator film are employed in an amount effective for detecting a color change thereby evidencing a change in pH. As used herein, the term "detection" denotes a color-change either visible by human eye having ordinary vision. Instrumentation may also be used. In some embodiments where the pH indicating moiety is embedded in the hydrophilic, hydronium ion penetrating layer, the pH indicating moiety is employed in an amount of about 0.01% w/w to about 10% w/w relative to the weight of that layer. In some embodiments the pH indicating moiety is employed in an amount of about 1% w/w to about 3% w/w.

In other embodiments, provided is a "sandwich" type of polymeric indicator film comprising:
  a) a first layer comprising one or more hydrophilic, hydronium ion penetrating layers;
  b) a second layer comprising one or more hydrophobic, water impermeable layers; and
  c) a pH indicator layer placed between the first layer and the second layer.

In some embodiments, the pH indicator layer comprises a sufficient amount of pH indicator moieties to provide visible color change in at least a portion of the polymeric pH indicator film upon contact with bacterial growth by-products.

In some embodiments, the pH indicator layer has a thickness of from 200 Angstroms to 5 microns.

In some embodiments, the polymeric indicator film further comprises an adhesive layer placed between the first hydrophobic, water impermeable layer and the pH indicator layer.

The adhesive layer may be any adhesive suitable for adhering the pH indicator(s) to the surface thereof, so that the pH indicator(s) form a separate layer over the adhesive. Preferably the adhesive is non-toxic (more preferably food grade safe) when dried and has a neutral or slightly basic pH, for example a pH not significantly above the pKa of the pH indicator applied, so that it does not interfere with the ability of the pH indicator to change color in the presence of bacterial growth. In some embodiments, the adhesive is a medical grade adhesive when the polymeric indicator is for medical application. In some embodiments, the adhesive is an adhesive that meet all standards as set forth by the FDA for food contact and/or food additives. In some embodiments, the adhesive is used in an amount such that the resulting polymeric film retains an uncolored, transparent nature at neutral pH.

FIG. 1 illustrates an example of the "sandwich" type of polymeric indicator film of this invention. In particular, polymeric indicator film 1 comprises an outer barrier layer polymer 3 which is a hydrophobic, water impermeable polymer as described herein. The outer layer 3 comprises a first and second surface, 3a and 3b respectively. In one embodiment, an adhesive layer 5 is applied to the second surface 3b of outer barrier layer 3. Application of the adhesive layer 5 can be conducted in any manner known in the art and the specific means for applying such a layer is not part of the invention. In one embodiment, the adhesive layer 5 can be applied by spraying an adhesive solvent system onto the second surface 3b. In another embodiment, the adhesive layer 5 can be applied by solvent casting wherein the solution of the adhesive and the solvent are applied to surface 3b (facing upward) and a conventional spreader is used to spread a uniform thickness of the solution to that surface followed by partial or complete drying of the solvent. Indicator layer 7 is applied in a manner likewise to that of adhesive layer 5 albeit each layer may be applied in the same or different manner. For example, indicator layer 7 can be applied by solvent casting and adhesive layer 5 can be applied by spraying. The inner or inside barrier layer 9 is then attached to the indicator layer 7 in such a manner that a cohesive laminated polymer indicator film 1 is formed. "Cohesive" as used herein means that visually, the laminated polymeric layered film will not readily separate and is viewed as a single film. Such polymeric indicator films can be prepared by the processes described in details below. It is understood that the terms "inner" and "outer" are used solely to differentiate the two layers. In one embodiment, the "inner" layer can be placed adjacent a food product such as raw meat such that the fluids from the meat contact the hydrophilic, hydronium ion penetrating layer of the film whereas the "outer" layer interfaces the environment where the meat is stored and as the outer layer is water impermeable, it retards water penetration through the film. In another embodiment such as when used as a catheter sheath, the "outer" layer may interface with the catheter surface while the "inner layer" will interface with the bodily fluids.

In one embodiment, the pH indicator is selected from the group consisting of hexamethoxy red and heptamethoxy red, and combinations thereof.

The pH indicating moieties detect pH change associated with by-products of bacterial growth. These by-products include, among others, gaseous carbon dioxide, hydrogen sulfide, sulfur dioxide, hydrogen, ammonium, lactate, and mixtures thereof. Mixtures of the by-product with moisture result in the formation of acids such as carbonic acid, sulfuric acid, ammonium hydroxide, lactic acid, or mixtures thereof that react with the indicator to produce a color change. The term "by-products" with reference to bacteria, refer to the gases that are expelled from the bacteria due to their natural growth of populations in numbers. Such gases can be in the vapor state or can combine with water or be hydrolyzed to form an acid such as sulfuric acid, carbonic acid, hydrogen sulfide or other gaseous or water vapor state which lowers the pH of the immediate environment with increasing concentrations of the gas vapor or water vapor combination.

In some embodiments, the acid is generated from a bacteria or is formed by reaction of a bacterial by-product with water, said bacterial by-product is selected from the group consisting of carbon dioxide and sulfur dioxide.

It is contemplated that in addition to bacteria, microbes detectable by the packaging materials include, among others, viral and fungal microbes. Among bacteria whose growth in food can be detected by the methods described herein include but are not limited to *Bacillus, Brucella, Campylobacter, Clostridium, Escherichia coli, Listeria monocytogenes, Salmonella, Streptococcus, Pseudomonas, Staphylococcus, Shigella* spp., *Vibrio* spp., *Yersinia* spp., coliform or spore forming bacteria and other food borne pathogens known to be involved in food contamination or a mixture of such microbes. Particular strains have been identified as associated with fresh vegetables. For example, *Escheria coli* O157:H7 was associated with prepackaged spinach: "Investigation of an *Escheria coli* O157:H7 Outbreak Associated with Dole Pre-Packaged Spinach," California Food Emergency Response Team Final Report, Mar. 21, 2007 (available from the California Department of Health Services, Food and Drug Branch, P.O. Box 997435, MS 7602, Sacramento, Calif. 95899-7435 and also available from U.S. Food and Drug Administration San Francisco District, 1431 Harbor Bay Parkway, Alameda, Calif. 94502.)

Food Spoilage Adaptation

The polymeric indicator films of this invention can be used on food or in bags or containers into which foods are placed to detect the presence of metabolic byproducts from bacteria.

Accordingly, in another aspect of this invention, provided is a food storage container containing a polymeric indicator film of this invention. In some embodiments the food storage container is a sealable bag. In other embodiments the food storage container is a jug or bottle for storing liquids.

In some embodiments, the polymeric indicator film is laminated. In this aspect of the present invention, the general approach to producing a laminate film is easily recognized and very well-known by those of ordinary skill in the art. One of ordinary skill may readily modify the teachings of the present specification to produce laminates comprised of numerous layers which will fall within the scope of the present invention.

In some embodiments, provided is a flexible wrap comprising an outer hydrophobic, water impermeable layer, an indicator layer wherein the indicator layer is as described herein and an inner hydrophilic, hydronium ion permeable layer. In some embodiments, the outer layer comprises one or more hydrophobic, water impermeable layers as described herein. In some embodiments, the hydrophobic, water impermeable outer layer of the polymeric indicator film is resistant to the passage of environmental and ambient gaseous compounds such as oxygen, hydrogen, nitrogen, moisture or other elements.

In some embodiments, provided is a pH indicating film or flexible wrap comprising an outer hydrophobic, water impermeable layer and an inner hydrophilic layer permeable to microbial byproducts and acids thereof, wherein sandwiched between the outer and inner layers is a plurality of pH indicating moieties selected from heptamethoxy red and hexamethoxy red or a combination thereof, and wherein the pH indicating moieties are entrapped within a polymer or are adherent to an adhesive, said pH indicating moieties and optionally the adhesive being situated between the outer and inner layers.

In some embodiments, the inner layer is permeable to microbial byproducts but impermeable to molecules having a molecular weight of about 200 daltons or more. Suitable inner barrier layers include polymeric films such as those found in Tegaderm™ (3M, St. Paul Minn.). In some embodiments, the inner barrier layer comprises one or more hydrophilic, hydronium ion penetrating layers described herein.

In some embodiments, outer layer comprises a hydrophobic, water impermeable layer described herein. In some embodiments, an adhesive layer is present on one surface of the outer barrier layer and the polymeric indicators are immobilized on the surface of the adhesive. In other aspects, the adhesive is a transparent, colorless (in the amount used) food safe adhesive. Suitable adhesive include Elmer's spray adhesive.

Suitable outer layers include polyethylene films, e.g., Glad® wrap or Saran™ wrap.

Suitable outer layers include the polyurethane films and films such as those used in Tegaderm™.

In some embodiments, the polymeric indicator film or flexible wrap has incorporated into, attached thereto or printed thereon a machine recognizable code such as a barcode or a RFID (radio frequency identification) tag.

Food or food stuff refers to any edible substance including solids and liquids such as meats, fish, vegetables, milk, milk products such as yogurt, cottage cheese, ice cream, etc., fruit and the like. Preferably, the food used in combination with the polymeric indicators of this invention are those which, when contaminated by microbes, provide for a detectable byproduct either from the food or the microbe that alters the pH of the food in a detectable manner.

As an alternative to an adhesive layer, the pH indicator can be cast onto the hydrophobic, water impermeable layer and/or the hydrophilic, hydronium ion penetrating layer using any number of different coating technologies, including: air knife coating, curtain coating, gap coating (knife over roll, knife over blanket, floating knife, etc.), gravure coating (engraved roll, offset engraved roll), immersion (dip) coating, mayer bar (meyer bar, metering rod, wire wound rod), reverse roll coating (L-head, nip-fed, pan-fed), rotary screen, or slot die (slot, extrusion). The choice of which coating technology might be selected to create the film is determined, in part, by the desired characteristics of the resulting film (i.e., film thickness). Other factors such as viscosity, surface tension, dry speed, production costs, etc., can also have a bearing on selection of which coating technology might be selected to create the film.

In some embodiments, the pH indicating moieties are placed as a separate layer between the hydrophilic, hydronium ion penetrating layer and the hydrophobic, water impermeable layer. In some aspects of these embodiments, the layer of pH indicating moieties is placed only over a portion of the film (for example) in the form of a warning (DO NOT EAT) which would be generated by the change in pH.

For the commercial practicability, a meyer bar coating technology may be employed where a 2 to 5 mil wet film thickness, and preferably, a 4.0 mil wet film thickness of the adhesive solution is applied to a polyethylene film.

A variety of configurations of the polymeric indicator film and pH indicating flexible wraps are provided. In one embodiment, the packaging material may be in the form of a roll of film that can be dispensed from a cardboard box having a cutting edge top and allowing for sheets of varying lengths to be dispensed and used for covering of certain products. In other embodiments the packaging material is dispensed from a large roll with heat sealability. In still other embodiments, the packaging material is in the form of a container or "baggie" with a resealable side or top and is used for storage of certain food products. Another configuration for the packaging material, a strip or polymer sheet or card comprising the polymeric indicator is inserted into the container.

For food spoilage, use of the indicators provided is based on the concept of pH change caused by the presence of bacterial metabolic by-products. The pH change can be caused by numerous sources, including: gases, liquids containing electrolytes, ions and molecules that influence pH like lactic acid, citric acid and ammonia. As the definition of pH is the negative log of the hydrogen ion concentration, used to express the acidity or alkalinity of a solution, moieties which effect this ionic concentration change may be detectable.

Some embodiments of the invention relate to the detection of by-products of contaminating bacterial growth in a packaged food product to provide an early warning of possible microbial growth occurring during storage in that package. These food products may be within the group commonly known as the low acid foods comprising meats, poultry, dairy, seafood and the like. These low acid foods have an inherent pH of near neutral or pH 7 or between pH 7.4 and 6.2. Foods known to be within the class referred to as medium acid foods are soups and pasta and have an inherent pH of 4.5 to 5.0. Foods that are known to be within the class referred to as acid foods are fruits and vegetables with an inherent pH between 3.7 and 4.5. Food known to be within the class referred to as high acid foods include lemons and pickled products with an inherent pH of between 2.3 and 3.7. In certain embodiments, food products other than those within the low acid range that have a more acidic characteristic may not be included in the applicable food product packaging for use with certain embodiments of this invention when the inherent lower pH values of the foods cause a reaction with the pH indicator of the packaging material and signal a false-positive result.

As hexamethoxy red and heptamethoxy red have significantly different pKa's (they change colors at different pHs), it is within the skill of the art to select the appropriate indicator relative to the acidity of the food stored within the polymeric indicator wrap of this invention.

Accordingly, in some embodiments provided is a method for detecting whether food is spoiled or contaminated by bacterial growth such that said food is not edible, said method comprising:
   a) placing a portion of said food proximal to the polymeric indicator film or pH indicating wrap;
   b) detecting the presence or absence of a colorimetric change in the polymeric indicator film or pH indicating wrap; and
   c) correlating the presence or absence of a colorimetric change in the polymeric indicator or pH indicating wrap to whether the food is non-edible or edible.

Medical Device Adaptation

In another aspect, provided are polymeric indicator films and pH indicating wraps for visually detecting bacterial growth in a medical setting, for example, related to wound dressings or catheter insertion sites. The presence of bacterial metabolic by-products is detected by a change in the color of the polymeric indicator film or pH indicating wraps positioned at or proximal to the site of wounds or catheter insertion sites.

In one aspect, the invention relates to wound dressings and methods for their use in detecting the by-products produced by bacterial growth. In some embodiments, the wound dressing comprises a polymeric indicator described herein.

In one embodiment, the wound dressing comprises indicators which are associated with the dressing in a manner to prevent leaching of the indicators from the dressing.

In one embodiment, the indicators are embedded in the wound dressing in a manner such that the indicator does not leach from the wound dressing. For example, the indicators can be placed as a layer sandwiched between the hydrophilic, hydronium ion penetrating polymer layer and the hydrophobic, water impermeable polymer layer.

The skin is the largest organ of the human body. One of the key functions that the skin performs is to protect the body's "insides" from the external environment by acting as a barrier and/or a filter between the "outside" and the "inside" of the body. The skin has other functions such as regulating the body's temperature and allowing for the excretion of some selected body wastes and toxins.

The acid/base balance is very important to metabolic health and plays a very important role in human physiology. The measure of acids and bases is conducted by determining the pH level, which is the inverse log of the hydrogen ion concentration. The pH scale or range is between 0 and 14 with 7 being neutral. Acids range between pH 0 to less than pH 7 and bases from above pH 7 to pH 14. pH 7 is defined as neutral—neither acidic nor basic. Weak acids are between pH 5.5 and less than pH 7 and weak bases between above pH 7 and pH 8.5.

The human skin pH is affected by numerous endogenous factors such as moisture, sweat concentrations, sebum, genetic predisposition and age. The skin contains pores, which are a combination of oil and sweat (sebaceous and sudoriferous) glands that assist in keeping the skin healthy. Skin secretions are a result of sweat or sebum secretion. In adolescents, there are often increased levels of sebum oil secretion stimulated by sex hormones. In general the normal excretion of oil and sweat from the skin's pores maintains a slightly acidic condition of approximately pH 5.5. The pH of normal, healthy surface skin is between pH 4.5 and pH 6. Some researchers have reported normal, healthy skin pH to be as low as pH 4 and as high as pH 6. Thus, the literature hosts a range for normal healthy skin pH values.

The skin acts as a protective mantel for the body and is sometimes referred to as the "acid mantel". The skin is the first defense mechanism against bacteria as the acidic skin condition provides an unfavorable environment for bacterial growth. This acidic defense varies with age. Typically newborns have a skin pH closer to neutral (pH 7) that quickly turns slightly acidic in order to protect the skin from bacterial growth. In the late teens and early 20's the acid mantle becomes well developed and provides an even better and more acidic defense against potentially harmful, external environmental factors. With the onset of old age the human skin can become more neutral in its pH and more susceptible to bacterial growth.

Differences in skin pH values have been evaluated in different races and gender. No significant differences have been reported between males and females although females were found to have a slightly lower skin pH than men. African-Americans were found to have a slightly more acidic stratum corneum (surface layer) than their Caucasian counterparts with respect to age. There is little variation in surface skin pH from one site on the body to another.

Provided are wound dressings comprising a polymeric indicator film described herein that are operational at skin pH and provide a color change, for example, colorless to colorful transition, which allows for facile visual detection of microbial contamination.

In one embodiment, provided is a wound dressing which comprises:
   a) a polymeric film having a top and bottom surface, said bottom surface for facing a wound site susceptible to bacterial contamination, which film comprises a hydrophilic, hydronium ion penetrating layer, a plurality of pH indicating moieties for indicating the presence of the bacterial growth by-products, said moieties being associated with or embedded within the hydrophilic, hydronium ion penetrating layer and said moieties change from colorless in the absence of a threshold level of bacterial by-products to colorful in the presence of a threshold level of bacterial by-products; and
   b) a hydrophobic, water impermeable layer adjacent to the top surface of said polymeric film.

In another embodiment, the indicating moieties are pH indicators and, preferably, are either hexamethoxy red or heptamethoxy red, more preferably, hexamethoxy red.

In another embodiment, the indicating moieties are associated with said polymeric film by forming a separate layer over the hydrophilic, hydronium ion permeable layer.

In another embodiment, the indicating moieties are associated with said hydrophilic, hydronium ion permeable layer by embedding said moieties within said layer such that said moieties are not capable of leaching therefrom.

In one embodiment, the pH indicating moieties are covalently bound to the hydrophilic, hydronium ion permeable layer.

The pH indicating moieties can be covalently linked, for example, to the hydrophilic, hydronium ion permeable film by coupling the functional groups on the pH indicators or introduced onto the indicators to complementary functional groups present on the film under reaction conditions suitable for forming the desired bonds. The pH indicators can also be synthetically modified to display the desired functional group for coupling to the polymer such as an aldehyde or an acyl group. Likewise, a polymeric surface can also be modified to present the desired functional group for coupling to the pH indicator. Another approach may be to sequester the pH indicator moieties within the matrix of the polymeric film, yet allowing the functionality of the pH indicator to remain intact.

In some embodiments, provided is a wound dressing which comprises:
a) an inner layer comprising one or more hydrophilic, hydronium ion penetrating layers;
b) an outer layer comprising one or more hydrophobic, water impermeable layers; and
c) a pH indicator layer placed between the inner layer and outer layer.

Uses of the wound dressings provided herein include placement proximate to wound sites susceptible to bacterial contamination in a manner wherein the hydrophilic, hydronium ion permeable layer is capable of contacting bodily fluids.

Wound sites susceptible to contamination by microorganisms including skin wounds, abrasions, burns, openings, surgical incision sites, puncture sites, and catheter insertion sites containing, for example, central venous catheter or other catheter used for insertion into the lumen of an artery or vein.

In one embodiment, provided is a method for detecting the presence of contaminating bacterial at a site susceptible to bacterial contamination, comprising covering the site with the wound dressings disclosed herein and monitoring the dressing for a color change.

By empirical data, growth of certain bacteria under controlled conditions may be correlated to pH such that the wound dressings described herein may be calibrated for different sensitivities (e.g., to show a colorimetric change at an earlier time) or for different types of bacteria.

Figure 2:
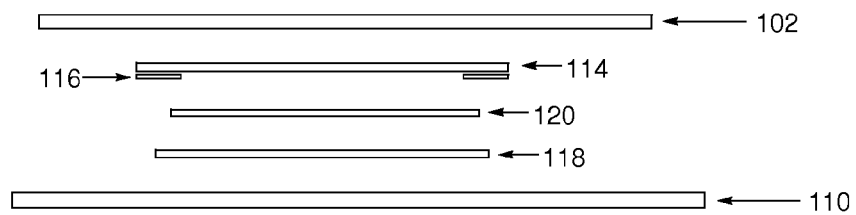
FIG. 2 illustrates an exploded side view of a wound dressing in accordance with an embodiment of the invention.
Figure 3:
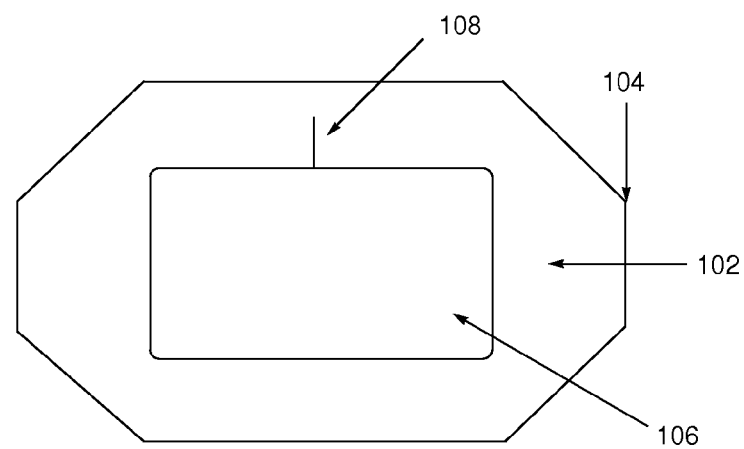
FIG. 3 illustrates a top view of the sheet liners 102 and 110 in accordance with an embodiment of the present invention.
Figure 3:
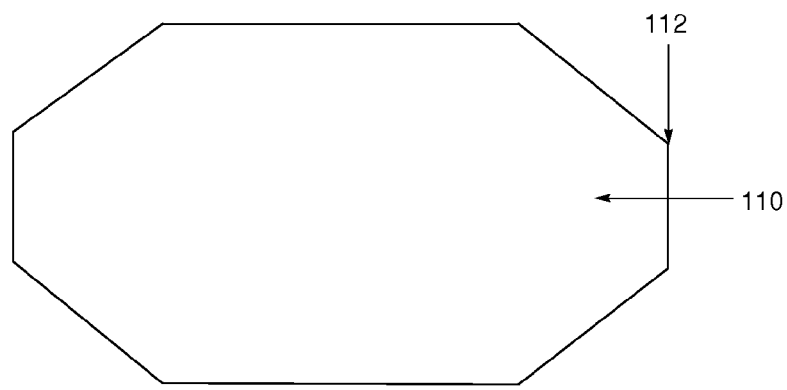

An example of a wound dressing is shown in FIGS. 2 and 3 having indicator layer 120 between a barrier membrane 114 and optionally a permeable membrane 118. An adhesive 116 is provided around the circumference of barrier membrane 114. Optionally, the wound dressing components can also be packaged between sheet liners 102 and 110 to facilitate their application to the skin.

In one example, barrier membrane 114 is a transparent, hydrophobic, and polymeric barrier membrane that acts as a barrier to the outside environment. Water, water vapor, and/or bacterial growth are prevented from penetrating to the wound or catheter insertion site from the environment by barrier membrane 114. Barrier membrane 114 does permit the passive diffusion of water vapor and oxygen from under the wound dressing or catheter insertion site to the environment. Barrier membrane 114 further permits the passive diffusion of oxygen from the environment through the barrier membrane to the skin and creates a moist environment at the surface of the skin and wound or catheter insertion site while limiting water vapor loss from the underlying tissue.

Barrier membrane 114 includes an adhesive 116 that is used to contact the skin and make a secure bond that is a perimeter of adhesion substantially along the border of barrier membrane 114. Adhesive 116 is a medical grade adhesive along the circumference/border of barrier membrane 114 and prevents the wound dressing from being dislodged or inadvertently removed from the skin.

Permeable membrane 118 is beneath (i.e., closer to the wound or catheter insertion site or skin) barrier membrane 114 and, in one example, is a transparent, hydrophilic polymeric membrane. Permeable membrane 118 does not extend fully to the margins of barrier membrane 114 but is held in place by adhesive 116 used to secure the wound dressing and indicator to the skin. Permeable membrane 118 is permeable to gases, water vapor, and gases dissolved in water vapor in one example. In yet another example, permeable membrane 118 is permeable to gases that include, oxygen, carbon dioxide, carbon monoxide, hydrogen sulfide, hydrogen, sulfur dioxide, lactic acid and ammonia among others, such that the concentration of gas which may ultimately diffuse through the polymeric composition is sufficient to produce a visual colorimetric reaction with indicator layer 120 that is easily visualized through barrier membrane 114, thereby alerting a user, such as an attending healthcare professional, of potentially harmful bacterial growth beneath the wound dressing at the catheter insertion site.

The polymers in the wound dressings disclosed herein can comprise substantial quantities of monomers having polar groups associated with them, such that overall polymeric composition is rendered hydrophilic. Preferably, the polymeric compositions are comprised of monomers which contain for example, hydroxyl groups, ester groups, amide groups, urethane groups, or carboxylate groups. While not being limited by way of theory, it is believed that the inclusion of polar groups allows water to more readily permeate the polymer and consequently, bring dissolved gases into proximity of the indicator contained within the two membranes and evoke a visible color change reaction.

Membranes 114 and 118 may be chemically/physically functionalized (e.g., to include different functional exchange groups with different backbone) to allow for selective control over passage through the membrane (e.g., to allow specific molecules to pass and/or for molecules to pass in a specific direction (e.g., away from or toward the wound site)).

The wound dressings can be packaged in various ways and in one embodiment is packaged similarly to a dressing apparatus trademarked as Tegaderm™, available from 3M Health Care Ltd., of St. Paul, Minn. Optionally, barrier membrane 114, indicator layer 120, and permeable membrane 118 may be packaged between sheet liners 102 and 110 to facilitate application of the wound dressing and indicator to the surface of the skin over the site of the indwelling central venous or other catheter.

In one example, sheet liner 102 is a thin and rigid sheet of thin card on the barrier side or top side of barrier membrane 114, with "wings" 104 at each end. Sheet liner 102 may include a window 106 pre-cut such that window 106 may be peeled away to reveal barrier membrane 114 underneath, thus leaving barrier membrane 114, indicator layer 120, and permeable membrane 118 suspended on a frame of sheet liner 102, which facilitates precise placement of the film and reduces wrinkling. Accordingly, window 106 may be peeled away and removed just prior to application of the film to the skin and allows for visualization of the catheter insertion site through the two transparent membranes 114 and 118 and indicator layer 120. Sheet liner 102 may also include a slit 108 along one side of the border of sheet liner 102 to allow for the peeling away of the border after the wound dressing is firmly applied to the skin at the site of the catheter insertion.

In a further example, sheet liner 110 is printed sheet of release paper coupled to the adhesive 116 adjacent to permeable membrane 118. Sheet liner 110 may also have wings 112 extending beyond the wings 104 of sheet liner 102 to aid in application to the skin. Sheet liner 110 is removed just after window 106 of sheet liner 102 is removed, and the wound dressing applied to the skin over the catheter site.

It will be apparent that the elements of the dressing that contact the skin, including but not limited to the barrier membrane, the adhesive, and the permeable membrane, are composed of medical grade materials and in one example meet the requirements for long-term skin contact as established by the United States Food and Drug Administration.

Indicator Preparation

A synthesis of heptamethoxy red or hexamethoxy red and a prophetic preparation of the polymeric indicator is shown in the Examples.

Preparation of the Polymeric Indicator Films

In another aspect provided herein is an improved method for preparing the pH indicating moieties according to the procedures disclosed herein.

In some embodiments, there is provided a process for preparing a polymeric indicator film comprising an inner hydrophilic, hydronium ion penetrating transparent layer and an outer hydrophobic, water impermeable transparent layer which process comprises:
- selecting one or more hydrophilic, hydronium ion penetrating layers as the inner layer of the polymeric film wherein the inner layer has a first and second surface;
- selecting one or more hydrophobic, water impermeable layers as the outer layer of the polymeric film wherein the outer layer has a first and second surface;
- applying a pH indicator layer to at least a portion of one surface of the outer layer; and
- bonding the inner and outer surfaces together such that the pH indicator layer is placed between the inner and outer layers.

In some embodiments, the process further comprises applying an adhesive layer to the one surface of the outer layer on which the pH indicator layer will be applied, which step is performed prior to application of the pH indicator layer.

In some embodiments, there is provided a process for preparing a polymeric indicator film comprising an inner hydrophilic, hydronium ion penetrating transparent layer and an outer hydrophobic, water impermeable transparent layer which process comprises:
a) selecting one or more hydrophilic, hydronium ion penetrating layers as the inner layer of the polymeric film wherein the inner layer has a first and second surface;
b) selecting one or more hydrophobic, water impermeable layers as the outer layer of the polymeric film wherein the outer layer has a first and second surface;
c) applying an adhesive layer to one surface of the outer layer;
d) applying a coating of pH indicator to at least a portion of the adhesive layer; and
e) bonding the inner and outer layers together such that the adhesive layer coated with the pH indicator is placed between the inner and outer layers, thereby forming the polymeric indicator film.

In some embodiments, the adhesive is partially dried before the coating of pH indicator is applied. In some embodiments, the outer layer with the indicator applied thereto is dried before binding of the outer layer with the inner layer.

In some embodiments, the pH indicator layer comprises a sufficient amount of pH indicator moieties to provide visible color change in at least a portion of the polymeric pH indicator film upon contact with microorganism growth.

In some embodiments, the pH indicator layer has a thickness of from about 200 Angstroms (Å) to about 5 microns.

Figure 4:
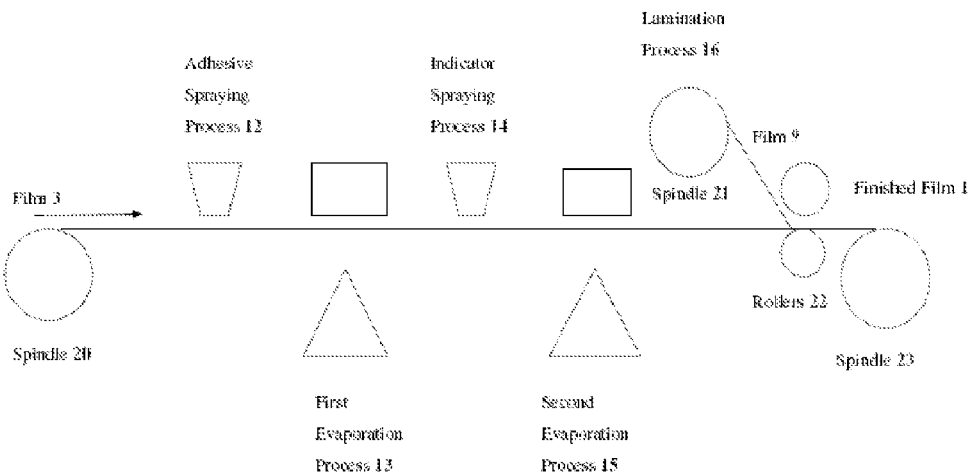
FIG. 4 illustrates a first example of a process for preparing the polymeric indicator film of FIG. 1.
Figure 5:
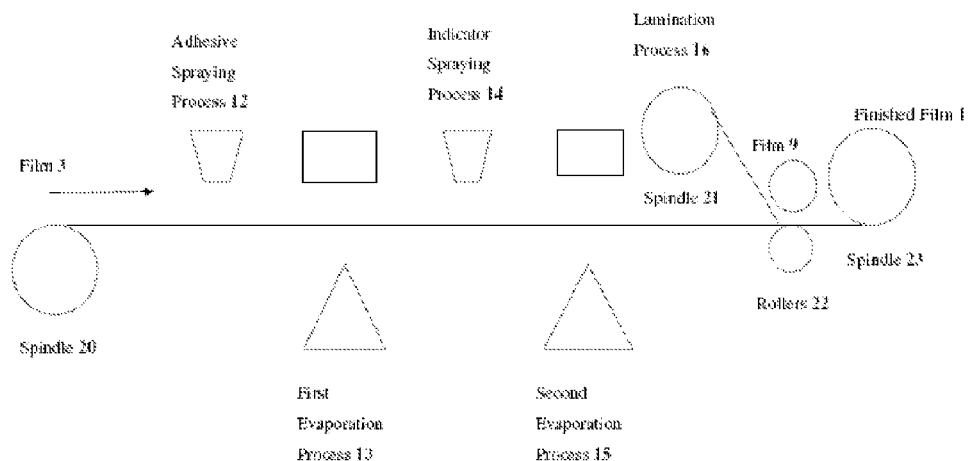
FIG. 5 illustrates a second example of a process for preparing the polymeric indicator film of FIG. 1.

In the manufacture process, the outer or inner film layers, preferably the outer layer, would serve as the base on a rolling stock production assemble and would feed through a line in which the adhesive spray is applied to one side of the film membrane, as illustrated in FIGS. 4 and 5. The adhesive spray would then be dried at controlled temperatures and time to evaporate off a portion, preferably a majority, of adhesive solvent carrier at which time the indicator (hexamethoxy red or heptamethoxy red) in an indicator solvent carrier is sprayed onto the surface of the drying adhesive in such a time, temperature and concentration to immobilize the indictor on the adhesive. The assembly then moves on to a second controlled temperature and time process to promote the evaporation of the indicator solvent carrier. Once an appropriate drying time and temperature are achieved, the outer or inner layer is then laminated to the immobilized indicator and adhesive with a slight pressure applied through the assembly rollers to assure complete lamination without wrinkles. Finally a release can be applied to the product to maintain the integrity of the laminated film and sandwich assembly. The final film sandwich product can be made ready for further packaging or wound dressing assembly.

In some embodiments the polymeric indicator film is for application as a food wrap. In some embodiments of the food wrap application, the width of the source roll and the finished film roll can be approximately twelve (12) inches to up to about 84 inches. In some embodiments, the finished polymeric indicator film can be collected and wound around the collection roll with the top side or interior side to the outside of the collection roll as seen in FIG. 4. In some embodiments, the finished product roll of film can be collected on and wound around the collection roll with the top side or interior side to the inside of the collection roll as seen in FIG. 5.

In some embodiments, a release liner may be introduced as a second laminate process just prior to the line being wound onto the finished film roll. In some embodiments, a release liner can be employed for added separation of the film as it is wound onto the collection roll.

The foregoing and other aspects of the embodiments disclosed herein may be better understood in connection with the following examples.

EXAMPLES

In the examples below as well as throughout the application, the following abbreviations have the following meanings. If not defined, the terms have their generally accepted meanings.

| | |
|---|---|
| ° C. = | degrees Celsius |
| DE = | Diatomaceous earth |
| ° F. = | Degrees Fahrenheit |
| g = | Gram |
| IPA = | Isopropyl Alcohol |
| kg = | Kilogram |
| L = | Liter |
| M = | Molar |
| ° C. = | Degrees Celsius |
| mbar = | Millibar |
| mg = | Milligram |
| min = | Minutes |
| mL = | Milliliter |
| MW = | Molecular Weight |
| m/z = | Mass/Charge |
| PE = | Polyethylene |
| PVOH = | Polyvinyl Alcohol |
| RT = | Room Temperature |
| w/w = | Weight to weight |

Example 1

Preparation of Heptamethoxy Red in Gram Scale

Step 1: Synthesis of Methyl 2,4,6-trimethoxybenzoate (CAS 29723-28-2)

2,4,6-trimethoxybenzoic acid (CAS 570-02-5) (5.61 g, 26.42 mmol) was suspended in 20 mL of methanol (CAS 67-56-1). Concentrated sulfuric acid (CAS 7664-93-9) (1 mL) was added to the mixture, and the reaction heated to reflux for 24 hrs. The reaction was cooled to room temperature, and the methanol (CAS 67-56-1) removed in vacuo. The residues were taken up in 50 mL 5% NaHCO$_3$ (CAS 144-55-8) and extracted with hexane (CAS 110-54-3) until all the solids had dissolved. The hexane extract was dried over anhydrous Na$_2$SO$_4$ (CAS 7757-82-6), filtered, and rotovapped to dryness to give the desired product, methyl 2,4,6-trimethoxybenzoate (CAS 29723-28-2), as a white crystalline solid.

Step 2: Synthesis of Heptamethoxy Red 1-bromo-2,4-dimethoxybenzene (CAS 17715-69-4) (4.23 g, 19.47 mmol) was added to a round bottom flask, and the flask flushed with nitrogen for 10 minutes. Anhydrous ether (CAS 60-29-7) (80 mL) was added, followed by the drop wise addition of n-butyllithium (CAS 109-72-8) in hexane (CAS 110-54-3) (1.6M, 12.2 mL). The cloudy mixture was stirred at room temperature for 10 minutes. Methyl 2,4,6-trimethoxybenzoate (CAS 29723-28-2) (2.20 g, 9.74 mmol) was dissolved in ether (CAS 60-29-7), and added drop wise to the reaction mixture. After the addition was complete, the reaction was stirred for 3 minutes longer. The reaction was then poured into a separatory funnel containing 5% NH$_4$Cl (CAS 12125-02-9) (50 mL) and shaken until a color change was observed. The layers were separated, and the ether layer was dried over anhydrous Na$_2$SO$_4$ (CAS 7757-82-6), filtered, and rotovapped to dryness. The crude oil was placed in the freezer. (6.02 g, 132% due to impurities).

Example 2

One Step Preparation of Heptamethoxy Red

Add (4.23 g, 19.47 mmol) 1-bromo-2,4-dimethoxybenzene (CAS 17715-69-4) to an appropriately sized round bottom flask. Attach a rubber septum to seal the flask.

Insert a needle into the septum as a vent and flush the round bottom flask with nitrogen for about 10 minutes.

Add (80 mL) anhydrous ether (CAS 60-29-7), followed by the drop wise addition of n-butyllithium (CAS 109-72-8) in hexane (CAS 110-54-3) (1.6M, 12.2 mL).

Stir the cloudy mixture for 10 minutes and keep the round bottom flask on ice.

Dissolve (2.20 g, 9.74 mmol) of methyl 2,4,6-trimethoxybenzoate (CAS 29723-28-2) in about 20 ml of anhydrous ether (CAS 60-29-7) (more than ~20 mL can be used if needed), and then add this drop wise to the reaction mixture.

After the addition is complete, stir the reaction mixture for about 3 minutes longer.

Pour the reaction mixture into a separatory funnel containing 5% NH$_4$Cl (aq) (CAS 12125-02-9) (50 mL) and shake until a color change is observed (pale orange).

The layers are allowed to separated, and dry the top ether layer with about 5 g anhydrous Na$_2$SO$_4$ (CAS #7757-82-6), filter, and rotovapped to dryness at 35-40° C. under 400 mbar.

Place the crude oil of heptamethoxy red (yellow-orange in color) into the freezer.

Yield is ~3.1 g.

Example 3

Preparation of Hexamethoxy Red in Gram Scale

Add (4.23 g, 19.47 mmol) 1-bromo-2,4-dimethoxybenzene (CAS #17715-69-4) to an appropriately sized round bottom flask.

Attach a rubber septum to seal the flask.

Insert a needle into the septum as a vent and flush the round bottom flask with nitrogen for about 10 minutes.

Add (80 mL) anhydrous ether (CAS #60-29-7), followed by the drop wise addition of n-butyllithium (CAS #109-72-8) in hexane (CAS #110-54-3) (1.6M, 12.2 mL).

Stir the cloudy mixture for 10 minutes and keep the round bottom flask on ice.

Dissolve (2.20 g, 9.74 mmol) of methyl 2,4-dimethoxybenzoate (CAS #2150-41-6) in about 20 ml of anhydrous ether (CAS #60-29-7) (more than about 20 ml can be used if needed), and then add this drop wise to the reaction mixture.

After the addition is complete, stir the reaction mixture for about 3 minutes longer.

Pour the reaction mixture into a separatory funnel containing 5% NH$_4$Cl (aq) (CAS #12125-02-9) (50 mL) and shake until a color change is observed (pale orange).

The layers are allowed to separated, and dry the top ether layer with about 5 g anhydrous Na$_2$SO$_4$ (CAS #7757-82-6), filter, and rotovapped to dryness at 35-40° C. under 400 mbar.

Place the crude oil of hexamethoxy red (yellow-orange in color) into the freezer.

Yield is about 3.1 g.

Example 4

Heptamethoxy Red in De for Addition to Blown Extruded Polyethylene Film

The following procedure describes the steps for incorporating 1% Heptamethoxy Red (HMR) via a 3% DE (DE=diatomaceous earth in PE pellets) load into about 200 feet of blown extruded PE (polyethylene) film.

The extruded PE film is about one (1) mil (0.001") thick× 48" wide with a DE load of up to 3% and about 1% Heptamethoxy Red in this example.

Step 1: Dilute 20 g of HMR with 40 g of ethanol to get a 33% solution of HMR in ethanol (20 g HMR+40 g ethanol=60 g of a 33% solution of HMR in ethanol).

Step 2: Take 60 g of a 33% solution of Heptamethoxy Red in ethanol and add it to 60 g of DE in a beaker on a hot plate over very low temperature using a stir bar and stir plate. Mix and heat slightly until the 40 g of ethanol evaporates leaving behind the 60 g of DE and 20 g of Heptamethoxy Red (therefore, gives 80 g of a 25% concentration Heptamethoxy Red in DE).

Step 3: Add the 80 g of the DE (containing a 25% concentration of Heptamethoxy Red) to the blown extrusion PE film line via the gravimetric fillers at a rate of 4% (w/w) which will provide for 1% HMR and 3% DE in the final blown PE film. Switch the gravimetric filler "On" which introduces the 4% (w/w) DE to the PE and within three minutes the blown extruded PE film coming out at the end of the blown extruder will have incorporated into it 1% HMR and 3% DE.

Example 5

Food Storage Bag Adaptation

This example illustrates a food storage bag for detecting the presence of bacterial metabolic byproducts.

Bag product manufacture and materials: The polymeric indicator of this invention may be manufactured as a bag or as part of a bag.

Bag product configuration for closure: The bag may be of a zip-lock type, or have another closure system allowing moisture to be trapped within the bag, so as to preserve the moisture of the food stuff.

Bag product size: Although any bag size may be used, this example is to illustrate a particular configuration for consumer use. For consumer-bagged spinach, a 48 ounce bag, optionally resealable, is fabricated. The bag may have optional clasps to reduce the inner volume if the consumer does not use the entire product at once. This will have the effect of concentrating any microbial byproducts which may be present or have arisen after the original opening of the bag. Local concentration of the microbial byproduct may have the ultimate effect of producing a stronger visual signal as the chromophores may be more readily available for ionic saturation.

Example 6

Polyethelene/Polyurethane Laminate

This example illustrates a polyethelene/polyurethane laminate joined by an adhesive containing a pH indicating moiety.

To a polyethylene sheet (Glad® Wrap) was sprayed Elmer's Multi-Purpose Spray Adhesive, 4 ounce, No E452. The spray adhesive dried in approximately five minutes after application and left a thin transparent film of the spray on the Glad® Wrap. The adhesive was clear after drying and did not have a negative effect on the flexibility characteristics of the Glad® Wrap film. The heptamethoxy red indicator in ethanol (5 mL) was lightly sprayed over the adhesive layer using a spray bottle, immobilizing the indicator on the surface of the adhesive. The composite was allowed to dry overnight.

The polyurethane films Tegaderm (3M) and 1 mil DT 1001 84 Shore A Polyether Polyurethane film (American Polyfilm Inc., Banford, Conn.) were used in the tests. The polyurethane film was applied to the polyethylene/adhesive/indicator assembly using a rolling pin. Dilute HCl was applied to the polyurethane films, resulting in a bright color change from colorless to violet red taking place slowly over a period of 12 to 16 hours.

Example 7

Synthesis of Polyethylene Film with Hexamethoxy Red

The following example demonstrates how to prepare a polyethylene film with hexamethoxy red associated therewith.

In this example, from 1-3% (w/w) PE/DE in pellet form is added to a blown extrusion line making a PE film that is 0.001 inch thick×48 inches wide. The blown extrusion process is adjusted such that it takes about ten (10) minutes for the gravimetrically fed PE/DE pellets entering the heated auger at the front end of the process to thoroughly mix with the PE and produce a 0.001 inch blown PE film coming out the back end of the process.

Line speed is adjusted and set to produce 120 feet of PE film per minute (at 0.001 inch thick×48 inches wide).

The amount of PE used during this production run will be about 1.0 kg per minute (or about 1.0 kg per 120 feet of extruded film) when following the above specifications for line speed, film thickness and film width. Dwell temperature for the ten (10) minutes in the auger is $\leq 420°$ F. (215° C.) and the hexamethoxy red is heat stable for this period of time at this temperature.

The PE blown extrusion process will start their normal supply of PE (with the gravimetric filler in the "Off" position). The gravimetric feeder will then be supplied with 700 g of PE/DE comprising sufficient amounts of hexamethoxy red so that the final concentration is 1% (w/w) and is set to add 1% (w/w) of the PE/DE to the PE being blown extruded.

Once the blown extrusion process is normalized and producing acceptable PE film, a switch is made to the gravimetric filler to the "On" position which begins to introduce 1% (w/w) PE/DE to the PE film and within about ten (10) minutes the blown extruded PE film coming out at the end of the pilot line will have incorporated into it the addition of the 1% (w/w) PE/DE.

2% (w/w) and 3% (w/w) compositions are likewise prepared.

Example 8

Synthesis of Polyurethane or Polystyrene Film with Hexamethoxy Red

The process of Example 7 is repeated except that PE is replaced with polyurethane (PU), polystyrene (PS) or any one of or combination of a number of different polymers where each polymer may provide a desired functionality.

Example 9

Preparation of a Polymeric Indicator Film as a Food Wrap

As shown in the FIG. 4 the food warp manufacturing process begins with a hydrophobic, water impermeable film 3, for example a polyethylene film such as Glad® wrap, which is the outer layer of the polymeric indicator film. The characteristic of the hydrophobic, water impermeable film 3 is its resistance to the passage of environmental and ambient gaseous compounds such as oxygen, hydrogen, nitrogen, moisture or other elements. The film 3 is brought to an adhesive spraying process 12, for example by the movement of the first spindle 20, where it is sprayed with an adhesive, preferably in a light spray or mist form. The adhesive may comprise one or more compounds in an aerosol. The film is then moved through the adhesive spraying process 12 to a first evaporation process 13 where an initial drying process of the adhesive begins. The adhesive may have a drying time of about five minutes at ambient temperatures and normal humidity conditions. The drying process may be accelerated by the addition of heat and/or forced airflow. The amount of drying can be controlled by the speed of the film through the first evaporation process 13, the temperature of the heat applied and/or the amount of forced air moved across the surface. The objective is to initiate evaporation of the carrier of the adhesive, such as acetone, while allowing the residual adhesive to accept the indictor, for example, a diluted heptamethoxy red used for the food warp application. The heat and/or forced air applied should be limited so as not to adversely affect the outer layer and/or the adhesive. A fume hood can be provided to collect the carrier vapors in a safe manner and dispose of the same in accordance with environmental regulatory requirements.

After the film has passed through the first evaporation process 13, it goes to the indicator spraying process 14 in which the adhesive receives an application of the indicator, for example, a dilute heptamethoxy red in a carrier, such as heptamethoxy red in 95% ethanol. The indicator is preferably applied in a light spray or mist form. The indicator heptamethoxy red in ethanol is applied to the surface of the drying adhesive in such a manner as to have the indicator immobilized on the surface of the drying adhesive. The film then passes though a second evaporation process 15 for evaporation of the carrier of the indicator. Heat and/or forced air may be applied to assist in the evaporation. The heat and/or forced air applied should be limited so as not to adversely affect the outer layer, the adhesive and/or the indicator. Once again a fume hood may be provided to collect the carrier vapors in a safe manner and dispose of the same in accordance with environmental regulatory requirements. Both the adhesive and the indicator are in the drying condition as the process moves into the lamination process 16. In the lamination process 16, a hydrophilic, hydronium ion penetrating film 9, which is the inner layer of the polymeric indicator film and may be supplied by the second spindle 21, is applied in a conventional method which carefully and gently presses the two layers together, for example by operation of rollers 22. The hydrophilic, hydronium ion penetrating film 9 may be a film with a relative high Moisture Vapor Transmission Rate (MVTR) such as Pebax® MV 3000 film. The residual adhesive should be sufficient to provide added laminate qualities to the film and contain the assembly as a "sandwich" containing the adhesive and immobilized indicator between the inner and outer layers. A second laminate process using a release liner, which is not shown in FIG. 4, can be applied to the film(s) just prior to collection on a finished polymeric indicator film 1 by the third spindle 23.

Example 10

Preparation of a Polymeric Indicator Film for Medical Application

As shown in FIG. 5 the manufacturing process of a polymeric indicator film for medical application begins with hydrophobic, water impermeable film 3. Preferably the hydrophobic, water impermeable film 3 used in a medical application is characterized by its passage of environmental and ambient gaseous compounds through the "barrier" such as oxygen, hydrogen, and nitrogen. The porosity of film 3 is such that it is resistant to the passage of a dipole molecule such as water. For example, film 3 may be a polyurethane film similar to that used by 3M™ in its Tegaderm™ product. Film 3 is brought to an adhesive spraying process 12, for example by the movement of the first spindle 20, where it is first sprayed with an adhesive, preferably in a light mist or spray form. The adhesive may comprise one or more compounds in an aerosol. The film then is moved through the adhesive spraying process 12 and on to a first evaporation process 13 where an initial drying process of the adhesive begins. The adhesive may have a drying time of about five minutes at ambient temperatures and normal humidity conditions. The drying process may be accelerated by the addition of heat and/or forced airflow. The amount of drying can be controlled by the speed of the film through the first evaporation process 13, the temperature of the heat applied and/or the amount of forced air moved across the surface. The objective is to initiate evaporation of the carrier while allowing the residual adhesive to accept the indictor, for example, a diluted hexamethoxy red used for the medical application. The heat applied should be limited so as not to adversely affect the outer layer and/or the adhesive. A fume hood can be provided to collect the carrier vapors in a safe manner and dispose of the same in accordance with environmental regulatory requirements.

After the film has passed through the first evaporation process 13, it goes to the indicator spraying process 14 in which the adhesive receives an application of the indicator, for example, a dilute hexamethoxy red in a carrier, such as ethanol. The indicator is preferably applied in a light spray or mist form. The indicator hexamethoxy red spray in ethanol is applied to the surface of the drying adhesive in such a manner as to have the indicator immobilized on the surface of the drying adhesive. The film then passes though a second evaporation process 15 to assist in the evaporation of the carrier of the indicator. Heat and/or forced air may be applied to assist in the evaporation. The heat and/or forced air applied should be limited so as not to adversely affect the outer layer, the adhesive and/or the indicator. Once again a fume hood may be provided to collect the carrier vapors in a safe manner and dispose of same in accordance with environmental regulatory requirements. Both the adhesive and the indicator are in the drying condition as the process moves into the lamination process 16. During the lamination process 16, hydrophilic, hydronium ion penetrating film 9, which is the inner layer of the polymeric indicator film and may be supplied by the second spindle 21, is applied in a conventional method which carefully and gently presses the two films together, for example by operation of the rollers 22. The film 9 may be a film with a relative high Moisture Vapor Transmission Rate (MVTR) such as Pebax® MV 3000 film or a polyurethane film with a high MVTR. The residual adhesive should be sufficient to provide added laminate qualities to the film and contain the assembly as a "sandwich" containing the adhesive and immobilized indicator between the inner and outer layers. A second laminate process using a release liner, which is not shown in FIG. 5, can be applied to the film(s) just prior to collection on finished polymeric indicator film 1 by the third spindle 23.

Additional rollers, which are not shown in FIGS. 4 and 5, may be used to support the film from above and/or below as it moves through the sequenced series of applications. These rollers can be employed not only to support the film from above and/or below but to mitigate any wrinkling of the film during the manufacturing processes.

Example 11

Application of a Polymeric Indicator Film on Food

A polymeric indicator film was each applied to a sample of ground beef contaminated with *Escherichia coli* (*E. coli*) of less than 100 colony forming units (CFUs) and to a sample of chicken contaminated with *Salmonella* of less than 100 CFUs at ambient conditions. Red color appeared on a significant portion of the polymeric indicator film within 18 hours. The following table summarized the results.

| Food | Color of the film at the time it was applied on the food | Color of the film 18 hours after it was applied on the food |
| --- | --- | --- |
| beef contaminated with *Escherichia coli* | clear | Deep red on a significant portion of the film |
| chicken contaminated with *Salmonella* | clear | Deep red on a significant portion of the film |

The embodiments and examples described above are not intended to limit the invention. It should be understood that numerous modifications and variations are possible in accordance with the principles of the present invention.

What is claimed is:

1. A wound dressing suitable for visibly detecting microorganism growth at a wound site based on a colorless to colorful transformation of the dressing, said dressing comprising:
   a) a barrier membrane forming a top surface of said wound dressing;
   b) a layer suitable for contacting bodily fluids from a wound site susceptible to microorganism growth which layer forms a bottom surface of said wound dressing; and c) pH indicators comprising a plurality of hexamethoxy red and/or heptamethoxy red, for indicating the presence of acidic growth by-products in said layer from contaminating microorganisms, and wherein said hexamethoxy red and/or heptamethoxy red pH indicators are colorless at neutral pH of 7 and in the absence of a threshold level of microorganism growth by-products to colorful in the presence of a threshold level of microorganism growth by-products.

2. The wound dressing of claim 1, wherein the microorganism growth by-products are bacterial growth by-products.

3. The wound dressing of claim 1, further comprising a permeable membrane adjacent to the bottom surface of the polymeric film.

4. The wound dressing of claim 1, wherein said barrier membrane is a transparent polymeric membrane.

5. The wound dressing of claim 3, wherein said permeable membrane is a hydrophilic, hydronium ion penetrating transparent polymeric film.

6. The wound dressing of claim 1, wherein said bottom surface suitable for contacting bodily fluids from a wound site comprises an absorbent pad.

* * * * *